(12) United States Patent
Tung et al.

(10) Patent No.: US 11,284,855 B2
(45) Date of Patent: Mar. 29, 2022

(54) ULTRASOUND NEEDLE POSITIONING SYSTEM AND ULTRASOUND NEEDLE POSITIONING METHOD UTILIZING CONVOLUTIONAL NEURAL NETWORKS

(71) Applicant: QISDA CORPORATION, Taoyuan (TW)

(72) Inventors: Yu-Teng Tung, Hsinchu (TW); Wei-Shin Hung, Hsinchu (TW)

(73) Assignee: Qisda Corporation, Taoyuan (TW)

( * ) Notice: Subject to any disclaimer, the term of this patent is extended or adjusted under 35 U.S.C. 154(b) by 114 days.

(21) Appl. No.: 16/733,247

(22) Filed: Jan. 3, 2020

(65) Prior Publication Data

US 2020/0245969 A1 Aug. 6, 2020

(30) Foreign Application Priority Data

Jan. 31, 2019 (CN) .......................... 201910099127.6

(51) Int. Cl.
*A61B 8/08* (2006.01)
*A61B 5/00* (2006.01)

(52) U.S. Cl.
CPC .......... *A61B 8/0841* (2013.01); *A61B 5/7267* (2013.01); *A61B 8/5207* (2013.01)

(58) Field of Classification Search
CPC . A61B 8/0841; A61B 8/5207; A61B 17/3403; G06T 2207/20084
See application file for complete search history.

(56) References Cited

PUBLICATIONS

Mwikirize, C., Nosher, J. L., & Hacihaliloglu, I. (2018). Convolution neural networks for real-time needle detection and localization in 2D ultrasound. International journal of computer assisted radiology and surgery, 13(5), 647-657. (Year: 2018).*
Pourtaherian, A. (2018). Robust needle detection and visualization for 3D ultrasound image-guided interventions. Technische Universiteit Eindhoven. (Year: 2018).*
Li X., Herranz L., Jiang S. (2016) Heterogeneous Convolutional Neural Networks for Visual Recognition. In: Chen E., Gong Y., Tie Y. (eds) Advances in Multimedia Information Processing—PCM 2016. PCM 2016. Lecture Notes in Computer Science, vol. 9917. Springer, Cham. (Year: 2016).*
Arash Pourtaherian et al., "Robust and semantic needle detection in 3D ultrasound using orthogonal-plane convolutional neural networks", May 31, 2018, International Journal of Computer Assisted Radiology and Surgery.

* cited by examiner

*Primary Examiner* — Amanda Lauritzen Moher
*Assistant Examiner* — Sean V Blinder

(57) ABSTRACT

An ultrasound needle positioning system includes an ultrasound probe and a processor. The ultrasound probe is used to capture a plurality of sets of needle insertion images. Each set of needle insertion images includes a plurality of needle insertion images corresponding to a needle body at a predetermined insertion angle. The processor is coupled to the ultrasound probe, and is used to train a first convolutional neural network according to at least one set of needle insertion images in the plurality of sets of needle insertion images to generate needle body positioning information after the needle body is inserted. The needle body positioning information includes a reference position, a length, and/or a width corresponding to the needle body at at least one predetermined insertion angle.

11 Claims, 11 Drawing Sheets

ULTRASOUND NEEDLE POSITIONING SYSTEM AND ULTRASOUND NEEDLE POSITIONING METHOD UTILIZING CONVOLUTIONAL NEURAL NETWORKS

CROSS REFERENCE TO RELATED APPLICATION

This non-provisional application claims priority of China patent application No. 201910099127.6, filed on 31 Jan. 2019, included herein by reference in its entirety.

BACKGROUND OF THE INVENTION

1. Field of the Invention

The invention relates to ultrasonic positioning technology, and specifically, to an ultrasound needle positioning system and an ultrasound needle positioning method utilizing convolutional neural networks.

2. Description of the Prior Art

Clinic ultrasound tests include non-invasive tests and invasive tests. The non-invasive tests employ needle puncturing to obtain tissues for cell analysis. Since it is not easy to observe a moving direction of a needle from an ordinary ultrasound image, ultrasound equipment can be optionally equipped with a needle guide or needle visualization function to assist a sonographer to observe how a needle advances towards a target location, thereby facilitating an associated health professional to perform biopsy and related treatments.

In the related art, a sonographer or associated health professional determines the location of a needle solely based on an ultrasound image, and therefore, false needle location determination happens frequently. Thus, there is a need for an ultrasound needle positioning system incorporating multi-angle ultrasound images, artificial intelligence decision and analysis to achieve a flexible, responsive and accurate needle guide functionality without using other equipment, and assisting a user to obtain a sample in clinical practice and apply treatments to affected parts more accurately.

SUMMARY OF THE INVENTION

In one aspect of the invention, an ultrasound needle positioning system including an ultrasound probe and a processor is provided. The ultrasound probe is used to capture a plurality of sets of needle insertion images. Each set of needle insertion images includes a plurality of needle insertion images corresponding to a needle body at a predetermined insertion angle. The processor is coupled to the ultrasound probe, and is used to train a first convolutional neural network according to at least one set of needle insertion images in the plurality of sets of needle insertion images to generate needle body positioning information after the needle body is inserted. The needle body positioning information includes a reference position, a length, and/or a width corresponding to the needle body at at least one predetermined insertion angle.

In another aspect of the invention, an ultrasound needle positioning method adopted in an ultrasound needle positioning system is disclosed. The ultrasound needle positioning system includes an ultrasound probe and a processor. The ultrasound needle positioning method includes: the ultrasound probe capturing a plurality of sets of needle insertion images, each set of needle insertion images including a plurality of needle insertion images corresponding to a needle body at a predetermined insertion angle; and the processor training a first convolutional neural network according to at least one set of needle insertion images in the plurality of sets of needle insertion images to generate needle body positioning information after the needle body is inserted. The needle body positioning information includes a reference position, a length, and/or a width corresponding to the needle body at at least one predetermined insertion angle.

In yet another aspect of the invention, an ultrasound needle positioning method adopted in an ultrasound needle positioning system is described. The ultrasound needle positioning system includes an ultrasound probe and a processor. The ultrasound needle positioning method includes: the ultrasound probe capturing a plurality of sets of needle insertion images, each set of needle insertion images including a plurality of needle insertion images corresponding to a needle body at a predetermined insertion angle; the processor training a first convolutional neural network according to at least one set of needle insertion images in the plurality of sets of needle insertion images to generate needle body positioning information after the needle body is inserted; the ultrasound probe capturing a plurality of sets of needle tip images, each set of needle tip images including a plurality of needle tip images corresponding to a plurality of predetermined rotation angles of a needle tip on the needle body; the processor training a second convolutional neural network according to at least one needle tip image and the needle body positioning information after the needle body is inserted, to generate needle tip positioning information corresponding to the at least one predetermined insertion; the processor receiving a target image and an insertion angle and a rotation angle of the target image; the processor utilizing the trained first convolutional neural network to generate needle body positioning information corresponding to the target image; and the processor utilizing the trained second convolutional neural network to generate needle tip positioning information corresponding to the target image. The needle body positioning information includes a reference position, a length, and/or a width corresponding to the needle body at at least one predetermined insertion angle.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
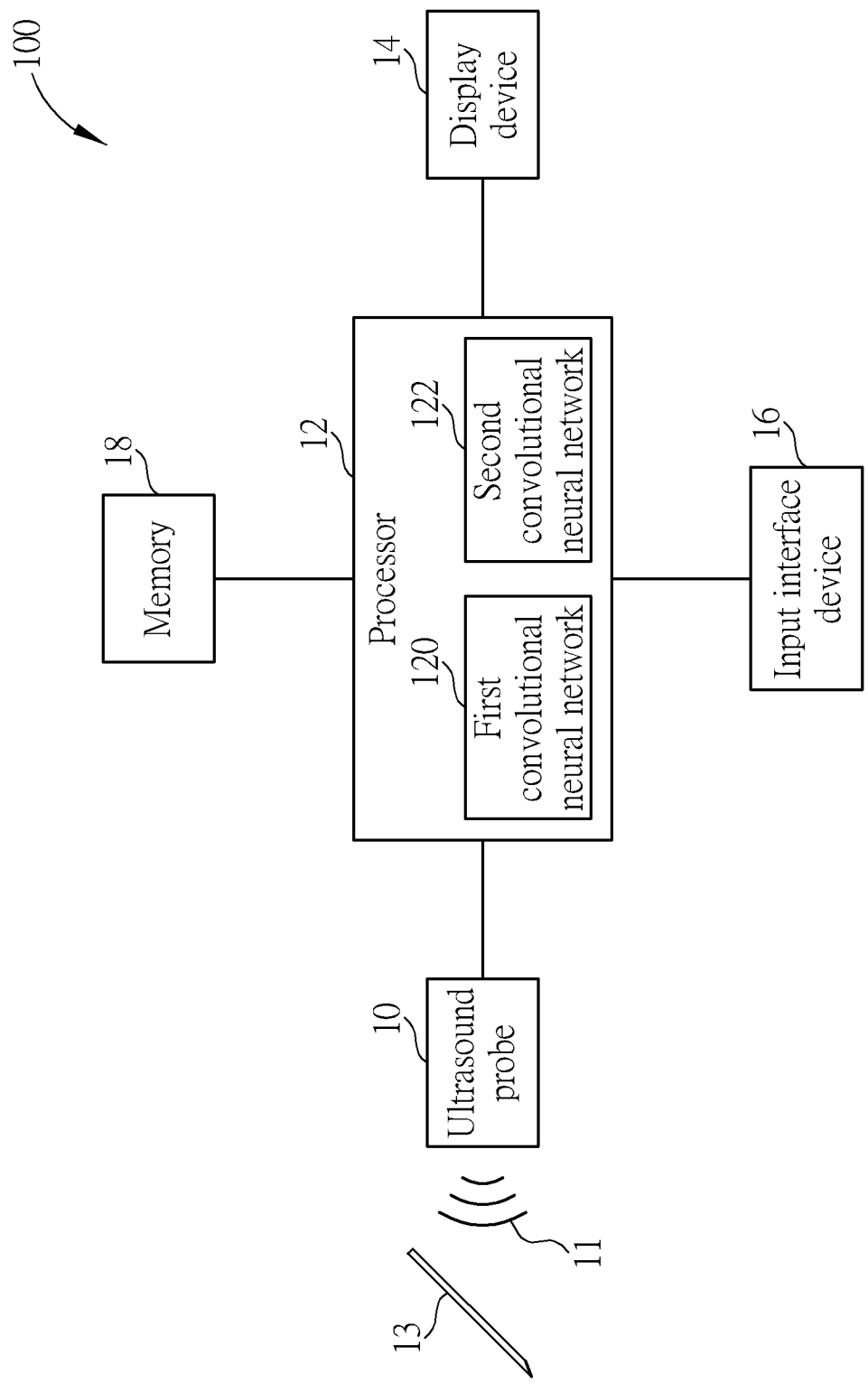
FIG. 1 is a block diagram of an ultrasound needle positioning system according to one embodiment of the invention.
Figure 2E:
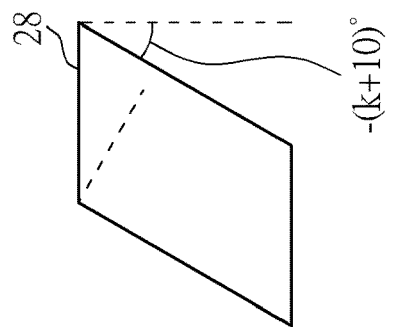
FIG. 2A through 2E are schematics diagram of a reference angle and an insertion angle of a needle body received by the ultrasound needle positioning system in FIG. 1.
Figure 2D:
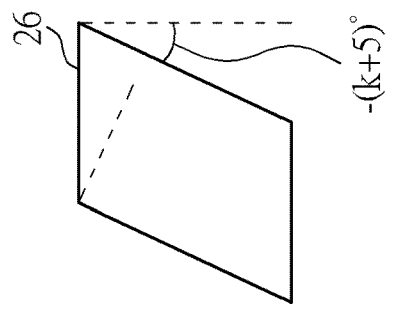
Figure 2C:
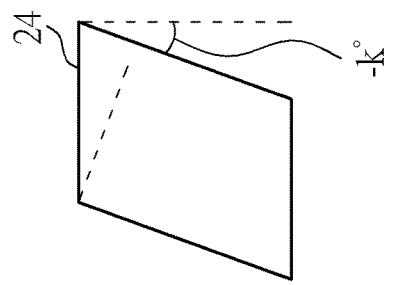
Figure 2B:
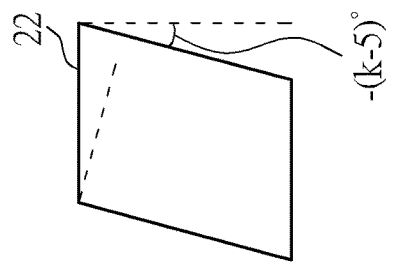
Figure 2A:
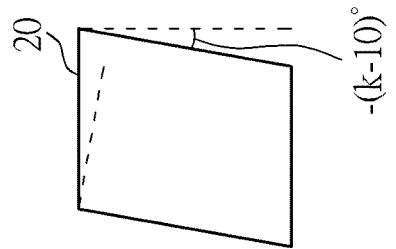

FIG. 1 is a block diagram of an ultrasound needle positioning system 100 according to one embodiment of the invention. The ultrasound needle positioning system 100 may comprise an ultrasound probe 10, a processor 12, a display 14, an input interface device 16 and memory 18. The processor 12 is coupled to the ultrasound probe 10, the display 14, the input interface device 16 and the memory 18. The processor 12 comprises a first convolutional neural network 120 and a second convolutional neural network 122. The number and functions of components in the ultrasound needle positioning system 100 are not limited to those provided in FIG. 1. For example, the ultrasound needle positioning system 100 may further comprise an image data system including needle insertion images, or the ultrasound needle positioning system 100 may not include the input interface device 16.

The ultrasound probe 10 comprises an ultrasound transceiver capable of transceiving an ultrasound signal and converting the same into an electrical signal, thereby capturing a plurality of sets of images of a needle body 13, or images of the needle body 13 inside an affected part of a patient. The plurality of sets of images may be a plurality of sets of needle insertion images of the needle body 13 or a plurality of sets of needle tip images. The memory 18 may be random access memory, cache memory, a hard drive, a flash drive or a combination thereof, and may store the plurality of sets of images of the needle body 13 captured by the ultrasound probe 10. The plurality of sets of images of the needle body 13 may be acquired by arranging the needle body 13 at a specific position and photographing the same by a system designer. The processor 12 may be a general-purpose processor, a central processing unit, an image processor, a graphics processing unit, a digital signal processor, a controller, an image processor, a specific application integrated circuit, a field programmable gate array, a digital circuit, an analog circuit, or a combination thereof. The processor 12 may train the first convolutional neural network 120 and the second convolutional neural network 122 according to the plurality of sets of images of the needle body 13, wherein the first convolutional neural network 120 may be used to position the needle body 13, and the second convolutional neural network 122 may be used to position a needle tip of the needle body 13. The first convolutional neural network 120 and the second convolutional neural network 122 may be two homogeneous neural networks or heterogeneous neural networks. The first convolutional neural network 120 and the second convolutional neural network 122 may form a more complicated neural network or a neural network having more layers. The processor 12 may further position the needle body 13 and the needle tip of the needle body 13 according to the trained first convolutional neural network 120, the trained second convolutional neural network 122 and a needle insertion image of the needle body 13. The processor 12 may be used to enhance the image of the needle body 13. The display 14 may be a liquid crystal display, a projector, a plasma display, a cathode-ray tube display, a printer, other visual display or a combination thereof, used to display an image of the needle body 13. The input interface device 16 may be a keyboard, a mouse, a touchscreen or a combination thereof, and used to receive information of a reference angle, and a positive or negative insertion angle and a rotation angle of a needle tip of the needle body 13 selected by a user. The succeeding paragraphs will provide details of the insertion angle and the rotation angle of the needle tip of the needle body 13.

FIGS. 2A to 2E are schematic diagrams of a reference angle k and insertion angles of the needle body 13 received by the ultrasound needle positioning system 100. FIGS. 2A to 2E indicate images 20 through 28 of 5 negative insertion angles. The images 20 through 28 respectively correspond to 5 negative insertion angles −(k−10), −(k−5), −k, −(k+5), −(k+10) of the needle body 13, and the reference angle represents an angle of a reference line displayed on the display 14, and can be, for example, 30, 15, 40 or other angles. When a needle guide function is enabled, the reference line may be used to guide a user to insert the needle body 13. If an angle between the reference line and an insertion line of inserting the needle body 13 is closer to a right angle, an ultrasound signal reflected from the needle body 13 will be more completely received by the ultrasound probe 10, resulting in a clearer image of the needle. If the angle between the reference line and the insertion line is less closer to a right angle and may be ±10, then the image of the needle is less clear. The images 20 through 28 respectively correspond to images of the negative insertion angles −(k−10), −(k−5), −k, −(k+5), −(k+10) with respect to the reference angle k of an ultrasonic wave transmission. Therefore, the images 20 through 28 may be regarded as including information of a plurality of insertion angles for use by the processor 12 to perform subsequent data analysis and determine the needle body positioning information of the needle body 13. The ultrasound needle positioning system 100 may perform pre-processing such as image dehazing, sharpening, contrast enhancement according to signal strengths, signal characteristics of the images 20 through 28, morphological characteristics and image features, and then analyze correlations between the images 20 through 28 using a machine learning method. After training with the plurality of images, the ultrasound needle positioning system 100 may determine a location of the needle body 13 using the neural network.

Figure 3:
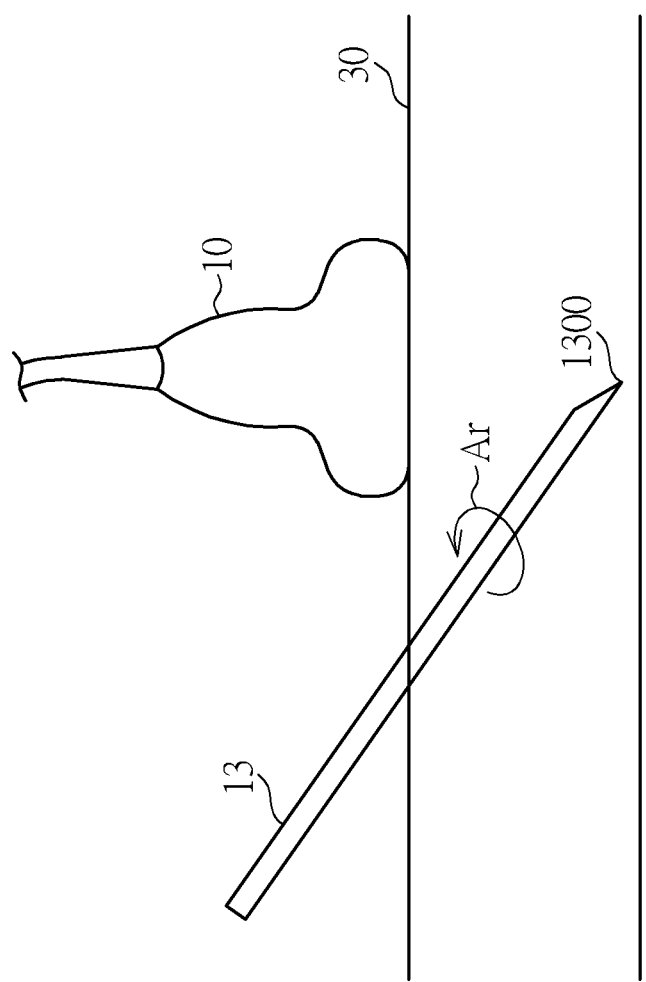
FIG. 3 is a schematic diagram of a rotation angle of a needle tip in the ultrasound needle positioning system in FIG. 1.

FIG. 3 is a schematic diagram of a rotation angle Ar of a needle tip of the needle body 13 in the ultrasound needle positioning system 100. As indicated in FIG. 3, the needle body 13 may puncture through a skin surface 30, and the ultrasound probe 10 may capture a needle tip image of the needle body 13 from the skin surface 30. The needle body 13 includes a needle tip 1300. The location of the needle tip 1300 changes as the needle body 13 rotates. Since the needle body 13 and the needle tip 1300 are two assembly components and can form an integrated device, the rotation angle Ar of the needle tip 1300 is just a rotation angle of the needle body 13. Therefore, the needle tip images corresponding to the needle body 13 having different rotation angles Ar of the needle tip may be used to determine the needle tip positioning information of the needle tip 1300.

Figure 4:
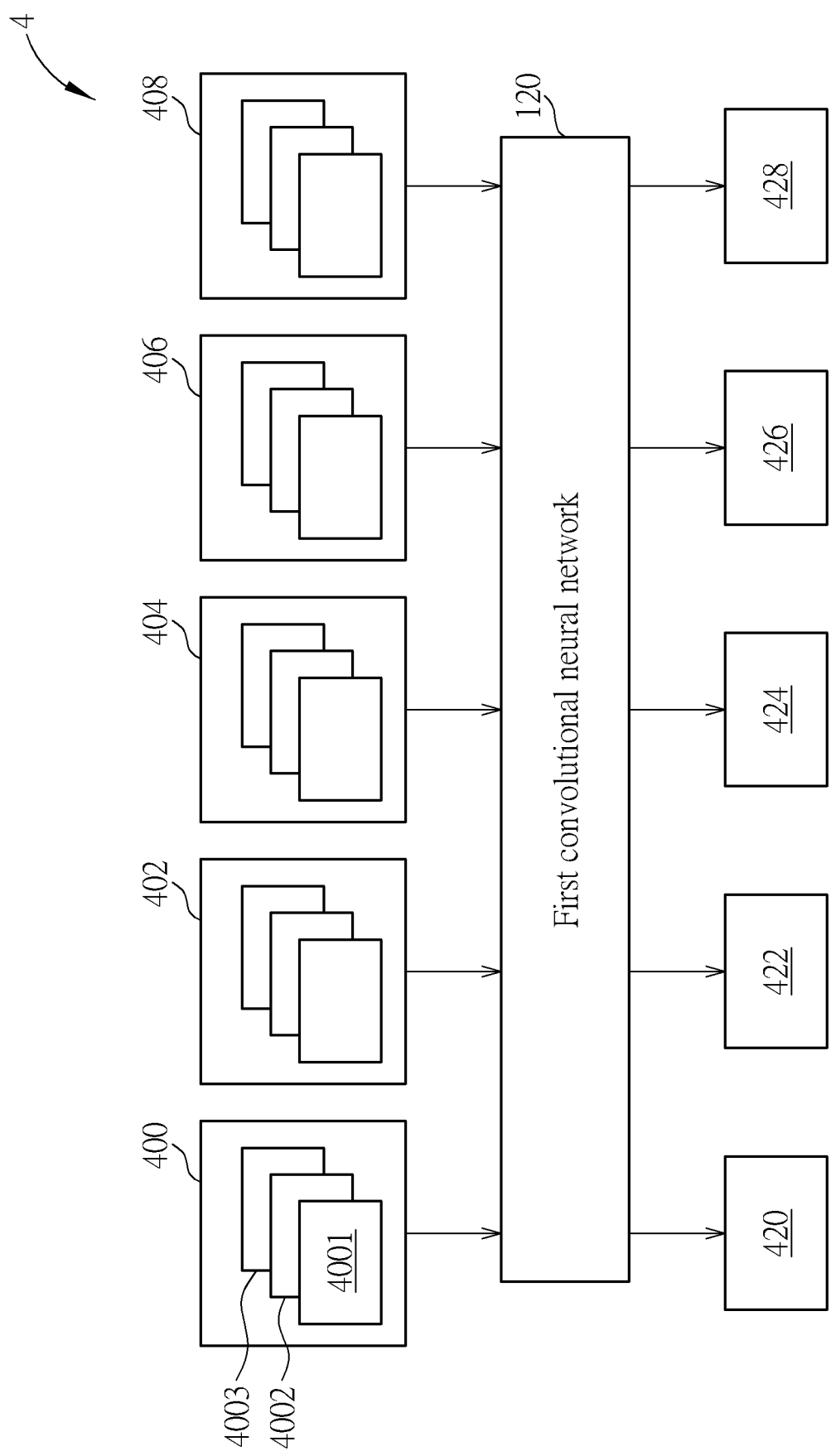
FIG. 4 is a schematic diagram of a training architecture of the ultrasound needle positioning system in FIG. 1.

FIG. 4 is a schematic diagram of a training architecture 4 of the ultrasound needle positioning system 100. The ultrasound needle positioning system 100 may be used to train the first convolutional neural network 120 to locate the needle body 13. The processor 12 may receive a plurality of sets of needle insertion images corresponding to a plurality of predetermined insertion angles, such as a plurality of sets of needle insertion images 400, 402, 404, 406 and 408 corresponding to the predetermined insertion angles −(k−10), −(k−5), −k, −(k+5), −(k+10) of the needle body 13. Each set of needle insertion images comprises a plurality of needle insertion images corresponding to the needle body 13 arranged at a predetermined insertion angle. For example, the needle insertion image set 400 comprises 3 needle insertion images 4001, 4002 and 4003 corresponding to the predetermined insertion angle −(k−10). The processor 12 may train the first convolutional neural network 120 according to at least one set of needle insertion images in the plurality of sets of needle insertion images to generate needle body positioning information after the needle body 13 is inserted. In particular, the processor 12 may train the first convolutional neural network 120 sequentially according to the plurality of sets of needle insertion images. For example, the processor 12 may train the first convolutional neural network 120 according to the plurality of sets of needle insertion images 400, 402, 404, 406 and 408 to sequentially generate needle body positioning information 420, 422, 424, 426 and 428 after the needle body 13 is inserted. The needle body positioning information after the needle body 13 is inserted includes a reference position, a length, and/or a width corresponding to the needle body 13 at at least one predetermined insertion angle. The reference position may be coordinates of a specific part of the needle body 13, such as coarse coordinates of the needle tip. The training architecture 4 may be used to train the first convolutional neural network 120 to generate coarse needle body positioning information after the needle body 13 is inserted at various insertion angles.

Figure 5:
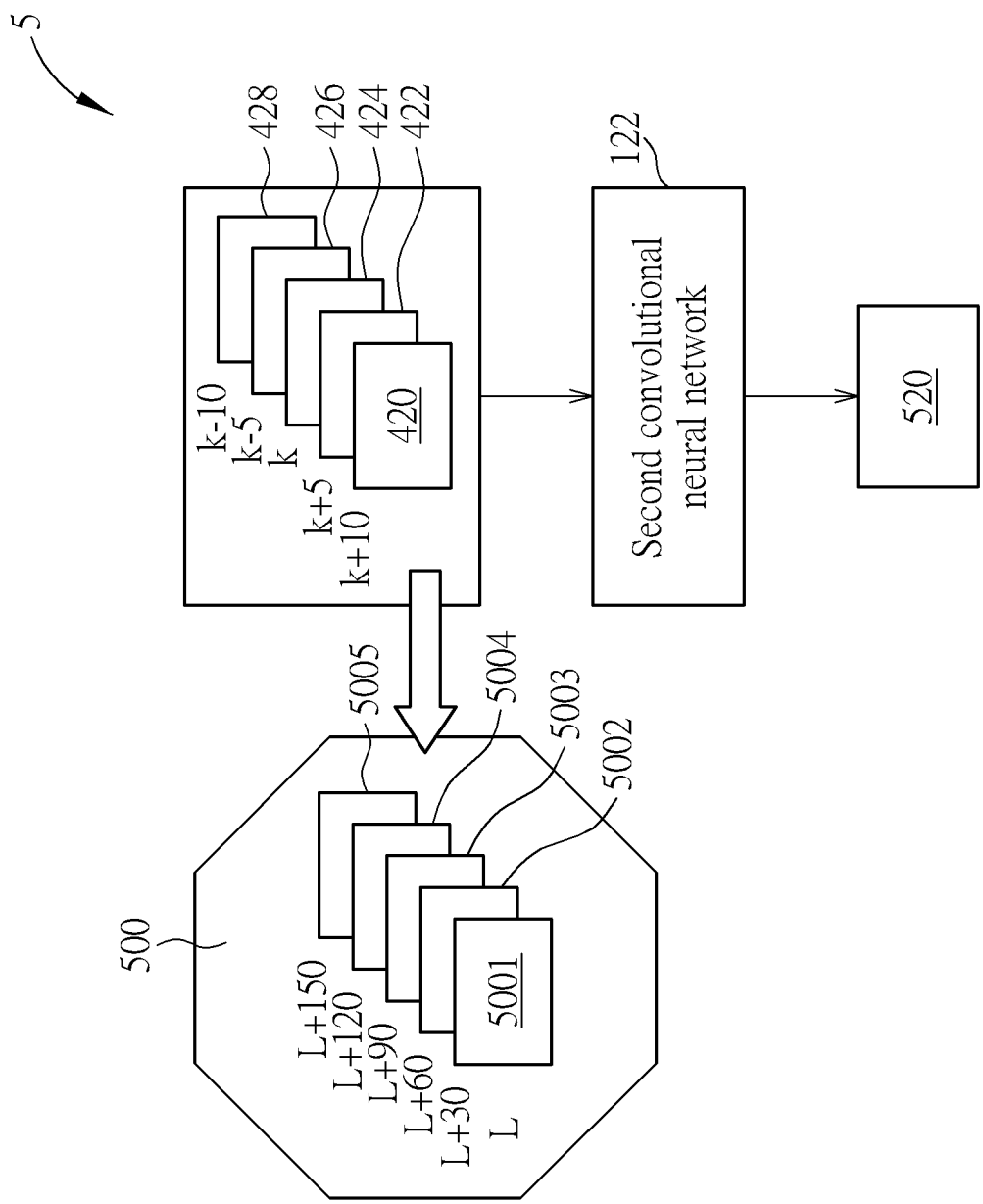
FIG. 5 is a schematic diagram of another training architecture of the ultrasound needle positioning system in FIG. 1.

FIG. 5 is a schematic diagram of a training architecture 5 of the ultrasound needle positioning system 100. The ultrasound needle positioning system 100 may be used to train the second convolutional neural network 122 to locate the needle tip 1300 on the needle body 13. The training architecture 5 employs a plurality of sets of needle tip images and the needle body positioning information generated by the training architecture 4 to train the second convolutional neural network 122. The processor 12 may receive a plurality of sets of needle tip images. Each set of needle tip images corresponds to a predetermined insertion angle of the needle body 13, and comprises a plurality of needle tip images corresponding to a plurality of predetermined rotation angles of the needle tip 1300 on the needle body 13. For example, the processor 12 may receive 5 sets of needle tip images corresponding to the plurality of predetermined insertion angles −(k−10), −(k−5), −k, −(k+5), −(k+10). A set of needle tip images 500 in the 5 sets of needle tip images may correspond to the predetermined insertion angle −(k−10), another set of needle tip images may correspond to another predetermined insertion angle, and so on. For brevity, only the set of needle tip images 500 is used in explanation. The set of needle tip images 500 comprises 5 needle tip images 5001, 5002, 5003, 5004 and 5005 respectively corresponding to 5 predetermined rotation angles L, (L+30), (L+60), (L+90), (L+120), (L+150) of the needle tip 1300 on the needle body 13. L is a reference rotation angle such as 0. The other 4 sets of needle tip images corresponding to the predetermined insertion angles −(k−5), −k, −(k+5), −(k+10) also comprise respective needle tip images at 5 predetermined rotation angles L, (L+30), (L+60), (L+90), (L+120), (L+150). Next, the processor 12 may train the second convolutional neural network 122 according to at least one needle tip image and the needle body positioning information after the needle body 13 is inserted, to generate needle tip positioning information of the at least one predetermined insertion angle corresponding to the needle body positioning information. For example, the processor 12 may train the second convolutional neural network 122 according to at least one of the plurality of needle tip images 5001 through 5005 in the set of needle tip images 500, and according to the needle body positioning information output by the first convolutional neural network 120 (such as the needle tip positioning information corresponding to −(k−10)), to generate the needle tip positioning information 520 corresponding to the predetermined insertion angle −(k−10) and the predetermined rotation angle L. The needle tip positioning information may be fine coordinates of the needle tip 1300. The training architecture 5 may be used to train the second convolutional neural network 122 to generate fine needle tip positioning information of the needle tip 1300 on the needle body 13.

Figure 6:
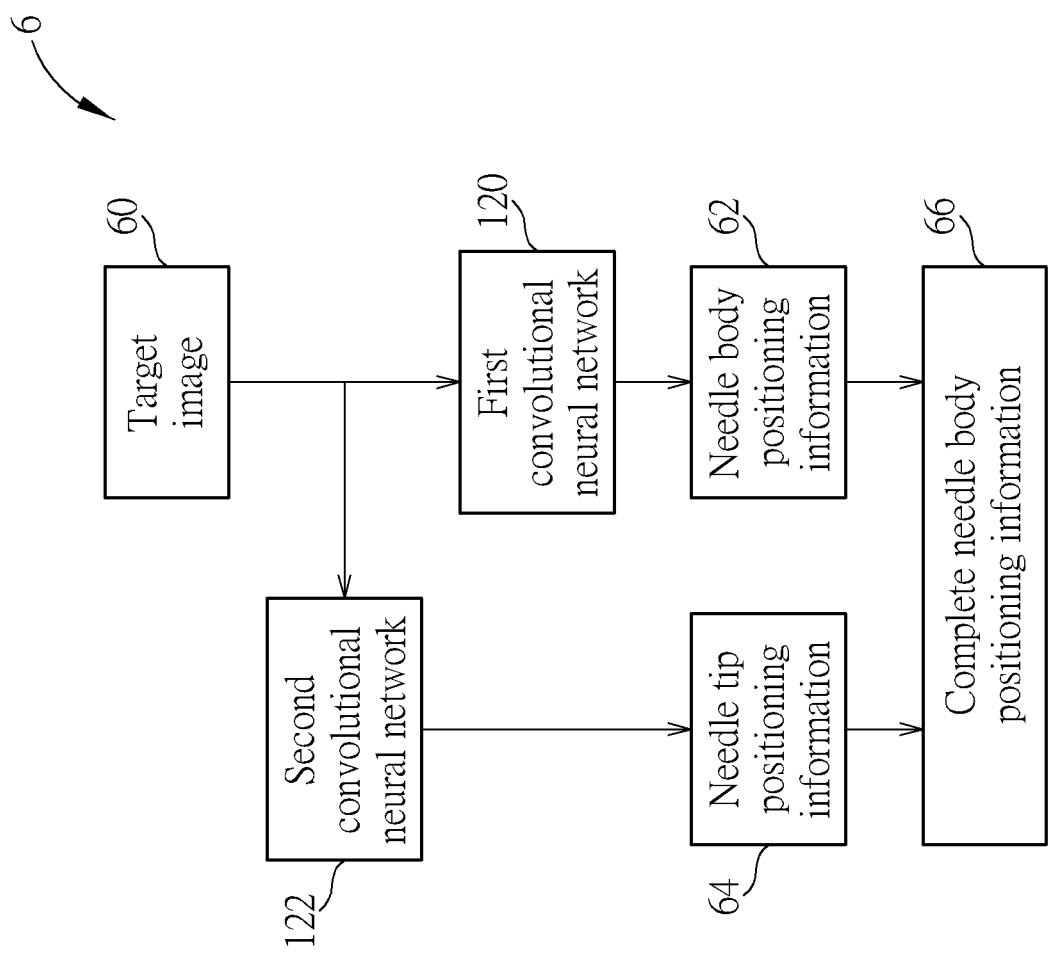
FIG. 6 is a schematic diagram of a prediction architecture of the ultrasound needle positioning system in FIG. 1.

FIG. 6 is a schematic diagram of a prediction architecture 6 of the ultrasound needle positioning system 100. The prediction architecture 6 may utilize the trained first convolutional neural network 120 and second convolutional neural network 122 to predict needle body positioning information and needle tip positioning information according to a target image 60. The target image 60 is an ultrasound image detected by the ultrasound probe 10. The processor 12 may receive the target image 60 and an insertion angle and a rotation angle of the target image 60, utilize the trained first convolutional neural network 120 to generate needle body positioning information 62 corresponding to the target image 60 according to the target image 60 and the insertion angle and the rotation angle of the target image 60, utilize the trained second convolutional neural network 122 to generate needle tip positioning information 64 corresponding to the target image 60. The processor 12 may combine the needle body positioning information 62 and the needle tip positioning information 64 to generate complete needle body positioning information 66 of the target image 60. The processor 12 may enhance a fuzzy image of needle-shaped area in the target image 60 according to the complete needle body positioning information 66, thereby providing needle enhancement for needle guide.

Figure 7:
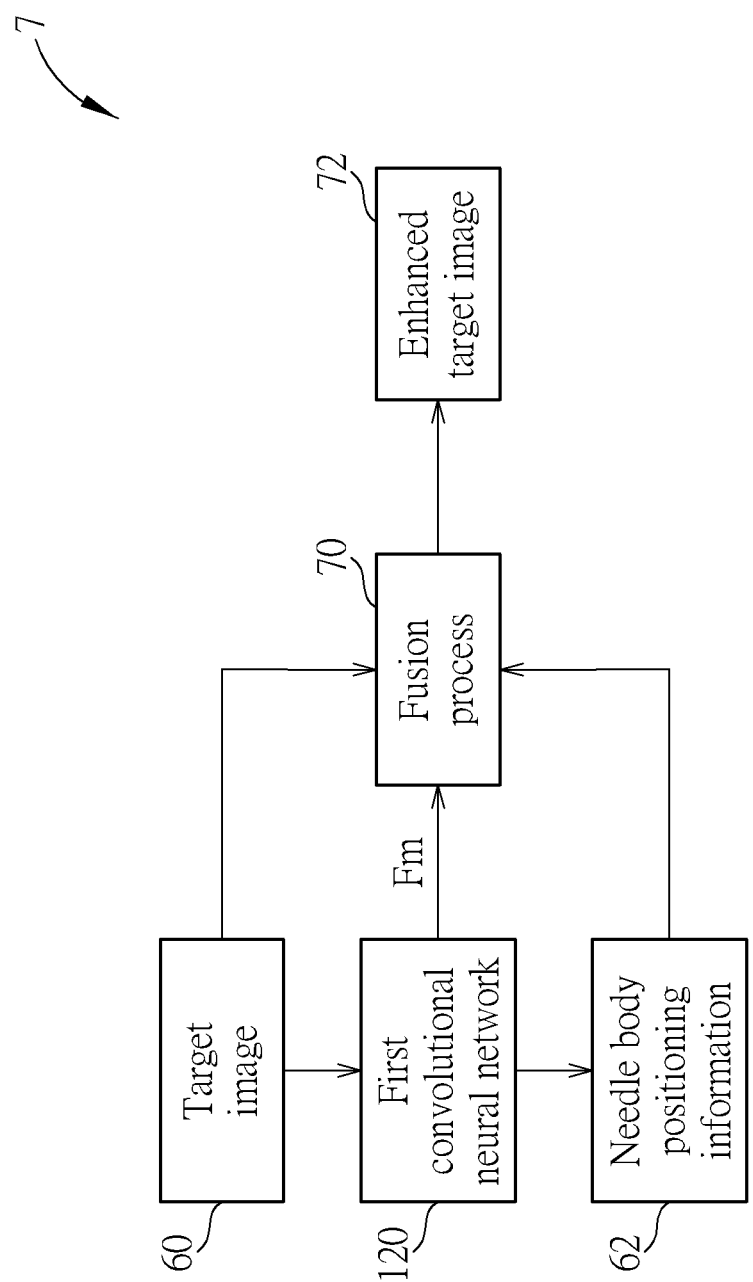
FIG. 7 is a schematic diagram of an image enhancement architecture of the ultrasound needle positioning system in FIG. 1.

FIG. 7 is a schematic diagram of an image enhancement architecture 7 of the ultrasound needle positioning system 100. As explained previously, the processor 12 may receive the target image 60 and an insertion angle and a rotation angle of the target image 60, and utilize the trained first convolutional neural network 120 to generate needle body positioning information 62 corresponding to the target image 60 according to the target image 60 and the needle insertion angle thereof. Furthermore, the processor 12 may acquire a plurality of multi-scale features Fm from the trained first convolutional neural network 120, and enhance the target image 60 according to the plurality of multi-scale features Fm and the needle body positioning information 62 of the target image 60 to perform fusion 70, so as to enhance the target image 60 to generate an enhanced target image 72. The plurality of multi-scale features Fm may comprise outline information of the needle body from each layer in the full-connected layer of the first convolutional neural network 120. The processor 12 may perform an enhancement process on the image of the needle body in the target image 60 according to the plurality of multi-scale features Fm, such as contrast enhancement, sharpening, or various sharpness enhancement processes. An artifact may be present in the target image 60. The artifact may be defined as an image having similar optical characteristics as those of the needle body, but should not be taken into consideration. Since the presence of the artifact is associated with the location of the outline of the needle body, the processor 12 may remove the artifact according to the outline of the needle body, as shown in the image enhancement architecture 8 in FIG. 8. The processor 12 may also apply a suitable filter to the target image 60 to enhance the target image 60 and remove the artifact from the target image 60.

Figure 8:
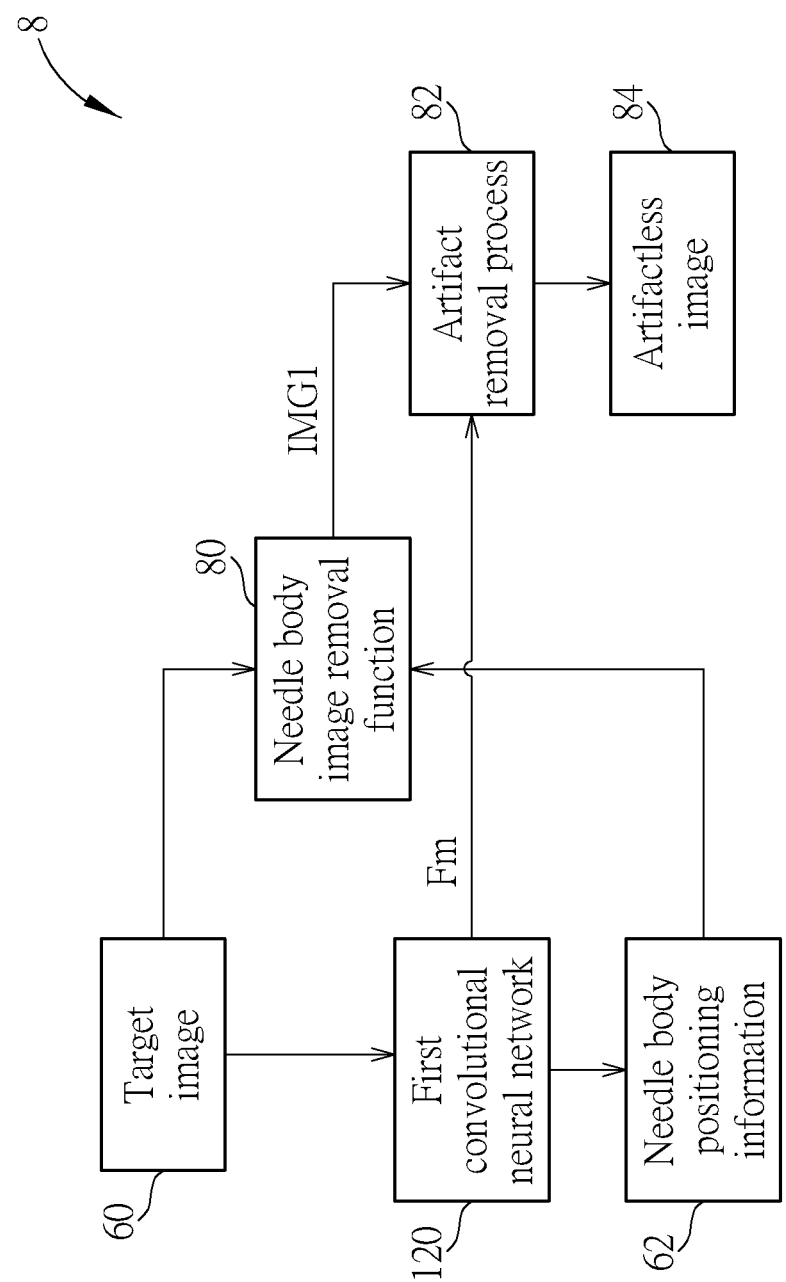
FIG. 8 is a schematic diagram of another image enhancement architecture of the ultrasound needle positioning system in FIG. 1.

FIG. 8 is a schematic diagram of an image enhancement architecture 8 of the ultrasound needle positioning system 100. The processor 12 may receive the target image 60 and an insertion angle thereof, and perform a needle body image removal function 80 according to the needle body positioning information 62 of the target image 60, so as to remove a needle-shaped image from the target image 60 to acquire a needleless image IMG1. The needleless image IMG1 can be regarded as an image with the real needle body 13 being removed therefrom and the artifact still being present therein. In order to remove the artifact, the processor 12 may acquire a plurality of multi-scale features Fm from the trained first convolutional neural network 120, so as to perform an artifact removal process 82. Specifically, the processor 12 may detect an artifact image in the needleless image IMG1 according to the plurality of multi-scale features Fm, and remove the detected artifact image from the needleless image IMG1 to generate an artifactless image 84. The plurality of multi-scale features Fm may comprise outline information of the needle body from each layer in the full-connected layer of the first convolutional neural network 120. Since the presence of the artifact is associated with the outline and location of the needle body, when performing the artifact removal process 82, the processor 12 may select an image close to the outline of the needle body in the needleless image IMG1 as a candidate image, and input the candidate image into the first convolutional neural network 120 using different sizes of sliding windows. Since the artifacts in the needleless image have similar features as those of the needle body, the first convolutional neural network 120 may generate needle body positioning information of the artifacts. Subsequently, the first convolutional neural network 120 may output the plurality of multi-scale features Fm including outline information of the artifacts to the artifact removal process 82. Since the artifacts may be present at a plurality of locations in the needleless image IMG1, when performing artifact removal process 82, the processor 12 may select a non-overlapping and most obvious artifact area according to the outline information of the artifacts, and reducing the selected artifact by filtering out the same. For example, the most obvious artifact area may be an image in the needleless image IMG1 having an outline and/or color tone and/or brightness closest to those of the needle body. After the processor 12 removes the artifact from the needleless image IMG1, an artifactless image 84 can be generated.

Figure 9:
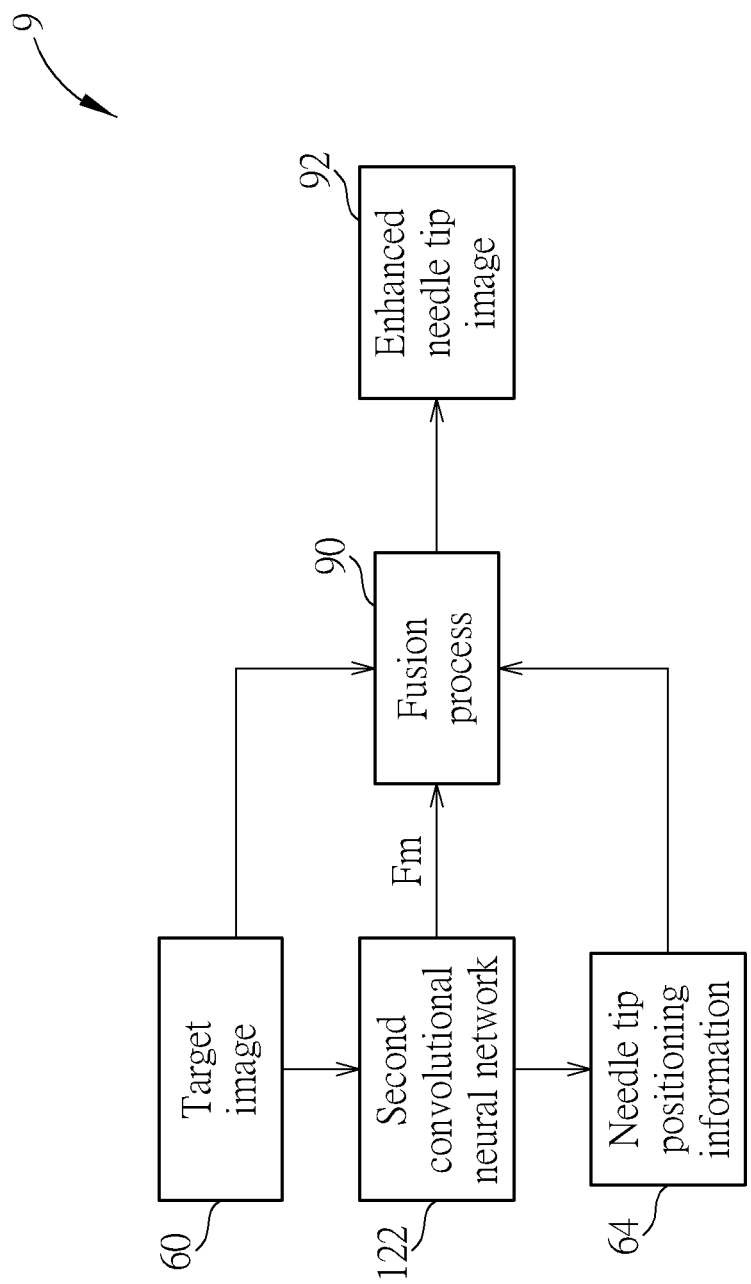
FIG. 9 is a schematic diagram of another image enhancement architecture of the ultrasound needle positioning system in FIG. 1.

FIG. 9 is a schematic diagram of an image enhancement architecture 9 of the ultrasound needle positioning system 100. The processor 12 may receive the target image 60 and an insertion angle and a rotation angle of the target image 60, and utilize the trained first convolutional neural network 120 to generate needle body positioning information 62 corresponding to the target image 60 according to the target image 60 and the needle insertion angle thereof. The processor 12 may further utilize the trained second convolutional neural network 122 to generate needle tip positioning information 64 corresponding to the target image 60 according to the target image 60, the body positioning information 62 thereof and the needle tip positioning information thereof. Next, the processor 12 may acquire a plurality of multi-scale features Fm from the trained second convolutional neural network 122, and perform a fusion process 90 on the target image 60 according to the plurality of multi-scale features Fm and needle tip positioning information 64 of the target image 60, so as to enhance the needle tip in the target image 60 and generate an enhanced target image 92. The plurality of multi-scale features Fm may comprise outline information of the needle tip from each layer in the full-connected layer of the second convolutional neural network 122. When performing the fusion process 90, the processor 12 may compute a linear combination of the plurality of multi-scale features Fm to optimize the enhanced needle tip image. For example, the outline information of the needle tip in the plurality of multi-scale features Fm may be first quantized and then averaged or weighted averaged. Next, the processor 12 may perform image enhancement on the target image 60 using the processed outline information of the needle tip. The image enhancement may be, for example, contrast enhancement, sharpening, or various sharpness enhancement processes, so as to generate the enhanced needle tip image 92. It should be understood that the process performed on the plurality of multi-scale features Fm is not limited to the linear combination, and may be using a non-linear function or interpolation/extrapolation to enhance reliability of the outline of the needle tip.

Figure 10:
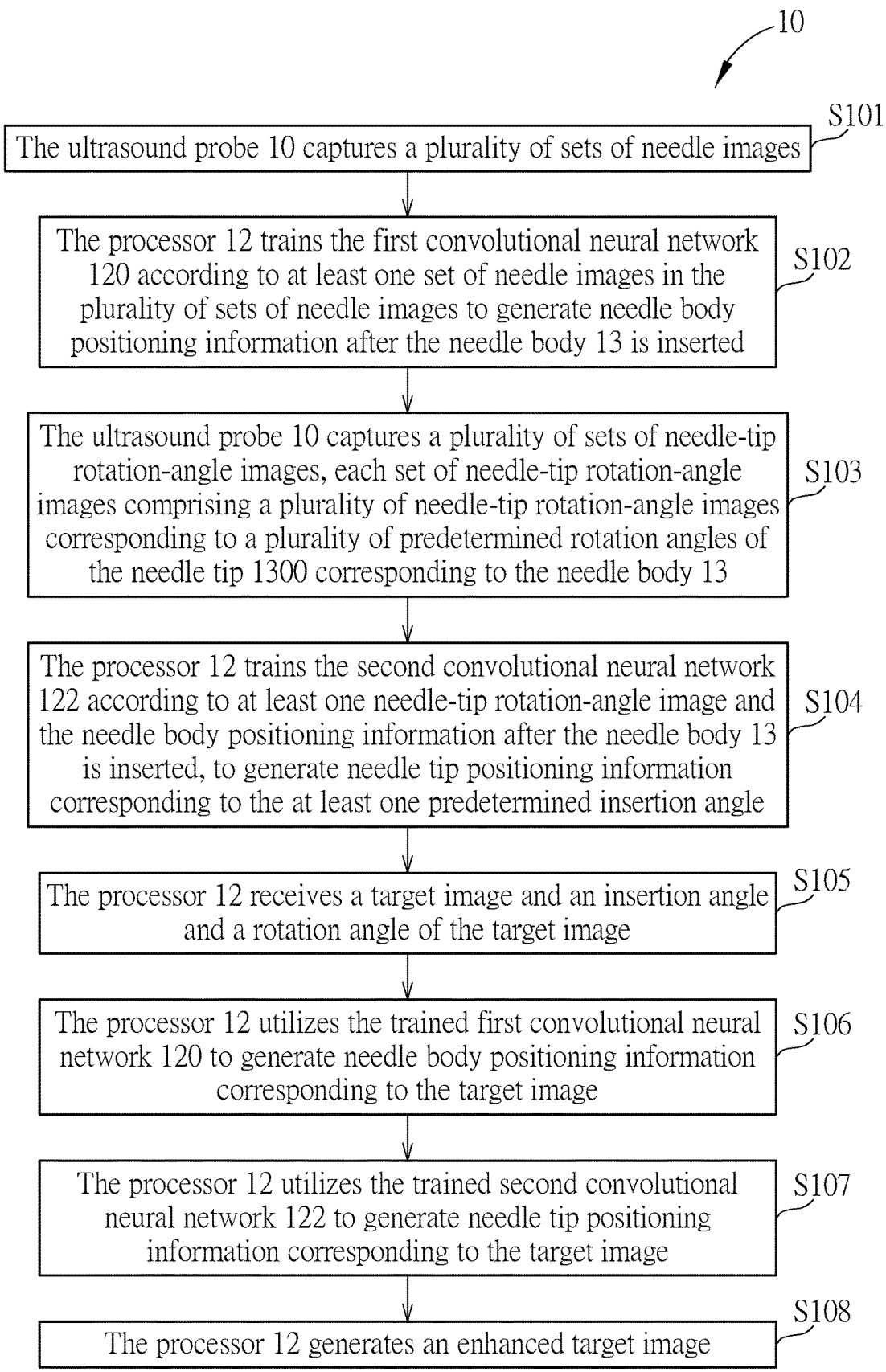
FIG. 10 is a flowchart of an ultrasound needle positioning method performed by the ultrasound needle positioning system in FIG. 1.

FIG. 10 is a flowchart of an ultrasound needle positioning method performed by the ultrasound needle positioning system 100. The ultrasound needle positioning system 100 may perform the ultrasound needle positioning method comprising Steps S101 through S108. Any reasonable technological change or step adjustment is within the scope of the disclosure. Steps S101 through S108 are explained as follows:

Step S101: the ultrasound probe 10 captures a plurality of sets of needle insertion images;

Step S102: the processor 12 trains the first convolutional neural network 120 according to at least one set of needle insertion images in the plurality of sets of needle insertion images to generate needle body positioning information after the needle body 13 is inserted;

Step S103: the ultrasound probe 10 captures a plurality of sets of needle tip images, each set of needle tip images comprising a plurality of needle tip images corresponding to a plurality of predetermined rotation angles of the needle tip 1300 corresponding to the needle body 13;

Step S104: the processor 12 trains the second convolutional neural network 122 according to at least one needle tip image and the needle body positioning information after the needle body 13 is inserted, to generate needle tip positioning information corresponding to the at least one predetermined insertion angle;

Step S105: the processor 12 receives a target image and an insertion angle and a rotation angle of the target image;

Step S106: the processor 12 utilizes the trained first convolutional neural network 120 to generate needle body positioning information corresponding to the target image;

Step S107: the processor 12 utilizes the trained second convolutional neural network 122 to generate needle tip positioning information corresponding to the target image;

Step S108: the processor 12 generates an enhanced target image.

Explanations for Steps S101 through S108 are provided in the preceding paragraphs and will not be repeated here for brevity. Steps S101 through S104 may be regarded as a convolutional neural network training stage adopted by the ultrasound needle positioning system 100. Steps S105 through S107 may be regarded as a stage adopted by the ultrasound needle positioning system 100 to utilize the trained convolutional neural network to perform needle tip positioning and needle body positioning according to the target image. Step S108 may be regarded as an image enhancement stage. As explained previously, any reasonable technological change or step adjustment is within the scope of the disclosure. For example, Step S108 may be omitted in some embodiments.

Figure 11:
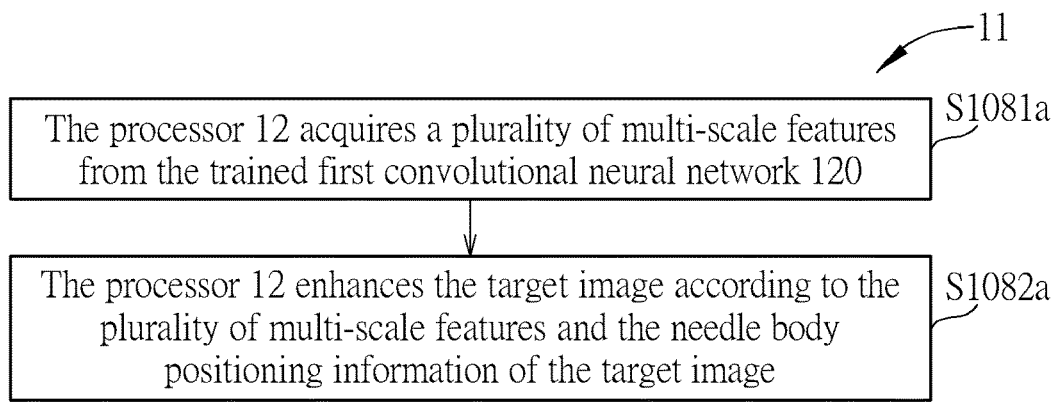
FIG. 11 is a flowchart of an image enhancement method in Step S108 in FIG. 10.

As explained previously, the image enhancement method in Step S108 may be needle body image enhancement, image enhancement relating to artifact removal, and/or needle tip image enhancement. The three image enhancement methods associated with Step S108 are detailed in the following paragraphs. FIG. 11 is a flowchart of an image enhancement method in Step S108 and performed by the ultrasound needle positioning system 100. FIG. 11 outlines a needle body image enhancement method and comprises Step S1081a through S1082a as follows:

Step S1081a: the processor 12 acquires a plurality of multi-scale features from the trained first convolutional neural network 120;

Step S1082a: the processor 12 enhances the target image according to the plurality of multi-scale features and the needle body positioning information of the target image.

Explanations for Steps S1081a and S1082a are provided in the preceding paragraphs and will not be repeated here for brevity. The needle body image in the target image may be enhanced by Steps S1081a and S1082a, and thus sonographers or related health professionals may clearly observe the needle body image on the target image.

Figure 12:
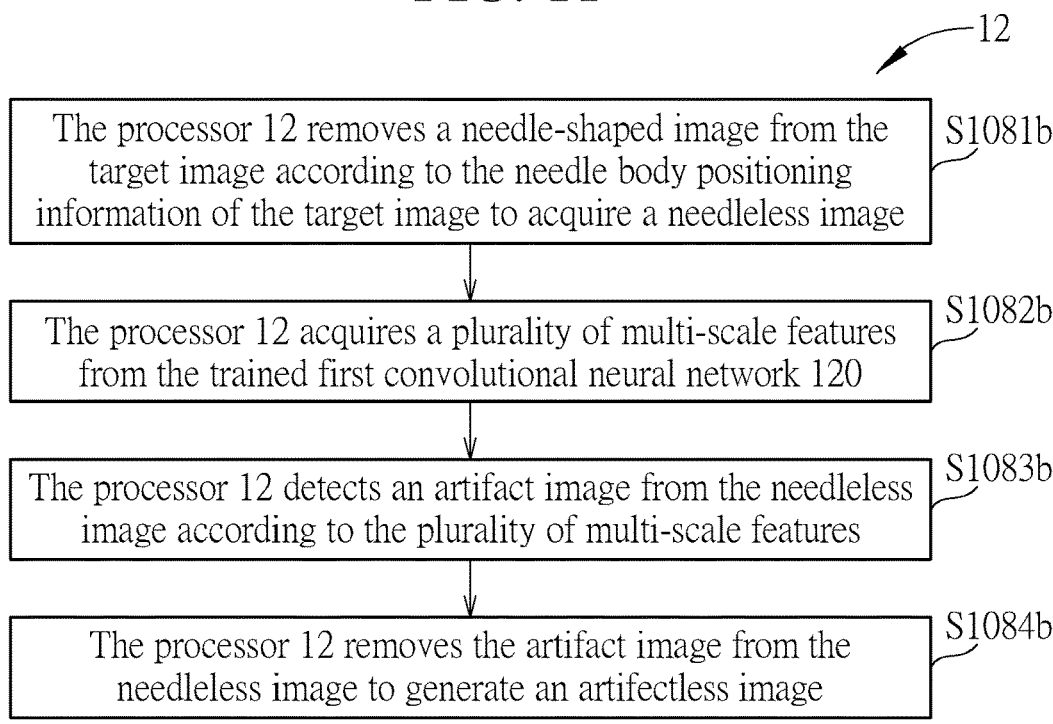
FIG. 12 is a flowchart of another image enhancement method in Step S108 in FIG. 10.

FIG. 12 is a flowchart of another image enhancement method in Step S108 adopted by the ultrasound needle positioning system 100. FIG. 12 outlines a process of removing artifacts, and comprises Step S1081b through S1084b as follows:

Step S1081b: the processor 12 removes a needle-shaped image from the target image according to the needle body positioning information of the target image to acquire a needleless image;

Step S1082b: the processor 12 acquires a plurality of multi-scale features from the trained first convolutional neural network 120;

Step S1083b: the processor 12 detects an artifact image from the needleless image according to the plurality of multi-scale features;

Step S1084b: the processor 12 removes the artifact image from the needleless image to generate an artifactless image.

Explanations for Steps S1081b through S1084b are provided in the preceding paragraphs and will not be repeated here for brevity. The artifact area in the target image may be removed by Steps S1081b through S1084b, and thus sonographers or related health professionals will not be misled by the image in the artifact area, thereby preventing a false operation.

Figure 13:
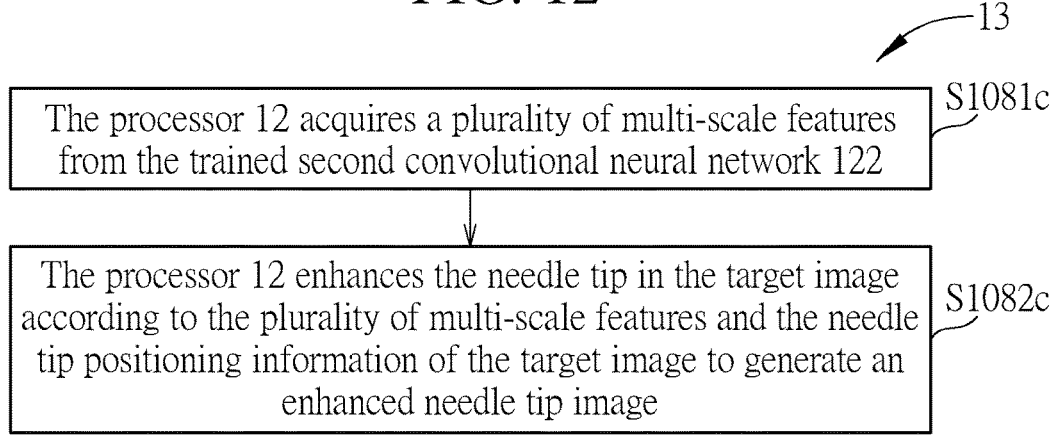
FIG. 13 is a flowchart of another image enhancement method in Step S108 in FIG. 10.

FIG. 13 is a flowchart of another image enhancement method in Step S108 adopted by the ultrasound needle positioning system 100. FIG. 13 outlines a needle tip image enhancement method and comprises Step S1081c and S1082c as follows:

Step S1081c: the processor 12 acquires a plurality of multi-scale features from the trained second convolutional neural network 122;

Step S1082c: the processor 12 enhances the needle tip in the target image according to the plurality of multi-scale features and the needle tip positioning information of the target image to generate an enhanced needle tip image.

Explanations for Steps S1081c and S1082c are provided in the preceding paragraphs and will not be repeated here for brevity. The needle tip image in the target image may be enhanced by Steps S1081c and S1082c, and thus sonographers or related health professionals may clearly observe the needle tip image on the target image.

As disclosed herein, the ultrasound needle positioning system and ultrasound needle positioning method according to the invention can provide a needle guide function without another device, and facilitate users such as sonographers or associated health professionals to obtain a sample in clinical practice more accurately and to apply treatments to affected parts. The ultrasound needle positioning system employs artificial intelligence technology to accurately locate a position of a needle according to image features of the needle, thereby reducing the risk of false determination of the needle location.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An ultrasound needle positioning system comprising:
an ultrasound probe configured to capture a plurality of sets of needle insertion images, and capture a plurality of sets of needle tip images, each set of needle insertion images comprising a plurality of needle insertion images corresponding to a needle body at a predetermined insertion angle, and each set of needle tip images comprising a plurality of needle tip images corresponding to a plurality of predetermined rotation angles of a needle tip on the needle body; and
a processor, coupled to the ultrasound probe, and configured to train a first convolutional neural network according to at least one set of needle insertion images in the plurality of sets of needle insertion images to generate a needle body positioning information after the needle body is inserted, and train a second convolutional neural network according to at least one needle tip image and the needle body positioning information after the needle body is inserted, to generate a needle tip positioning information corresponding to the at least one predetermined insertion angle;
wherein the needle body positioning information includes a reference position, a length, and/or a width corresponding to the needle body of at least one predetermined insertion angle;
the processor receives a target image and an insertion angle and a rotation angle of the target image, utilizes the trained first convolutional neural network to generate, according to the target image, the insertion angle and the rotation angle, a needle body positioning information corresponding to the target image, and utilizes the trained second convolutional neural network to generate a needle tip positioning information corresponding to the target image; and the processor removes a needle-shaped image from the target image according to the needle body positioning information of the target image to acquire a needleless image, acquires a plurality of multi-scale features from the trained first convolutional neural network, detects an artifact image from the needleless image according to the plurality of multi-scale features, and removes the artifact image from the needleless image to generate an artifactless image.

2. The system of claim 1, wherein:
the first convolutional neural network and the second convolutional neural network are two homogeneous neural networks or heterogeneous neural networks.

3. The system of claim 1, wherein the processor acquires a plurality of multi-scale features from the trained first convolutional neural network, and enhances the target image according to the plurality of multi-scale features and the needle body positioning information of the target image to generate an enhanced target image.

4. The system of claim 3, wherein the plurality of multi-scale features from the trained first convolutional neural network comprise outline information of the needle body.

5. The system of claim 1, wherein the processor acquires a plurality of multi-scale features from the trained second convolutional neural network, and enhances the needle tip of the target image according to the plurality of multi-scale features and the needle tip positioning information of the target image to generate an enhanced needle tip image.

6. The system of claim 5, wherein the processor computes a linear combination of the plurality of multi-scale features from the trained first convolutional neural network to optimize the enhanced needle tip image.

7. An ultrasound needle positioning method comprising:
an ultrasound probe capturing a plurality of sets of needle insertion images, each set of needle insertion images comprising a plurality of needle insertion images corresponding to a needle body at a predetermined insertion angle;
a processor training a first convolutional neural network according to at least one set of needle insertion images in the plurality of sets of needle insertion images to generate a needle body positioning information after the needle body inserted;
the ultrasound probe capturing a plurality of sets of needle tip images, each set of needle tip images comprising a plurality of needle tip images corresponding to a plurality of predetermined rotation angles of a needle tip on the needle body;
the processor training a second convolutional neural network according to at least one needle tip image and the needle body positioning information after the needle body is inserted, to generate needle tip positioning information corresponding to the at least one predetermined insertion angle;

the processor receiving a target image and an insertion angle and a rotation angle of the target image;

the processor utilizing the trained first convolutional neural network to generate, according to the target image, the insertion angle and the rotation angle, a needle body positioning information corresponding to the target image;

the processor utilizing the trained second convolutional neural network to generate needle tip positioning information corresponding to the target image;

the processor removing a needle-shaped image from the target image according to the needle body positioning information of the target image to acquire a needleless image;

the processor acquiring a plurality of multi-scale features from the trained first convolutional neural network;

the processor detecting an artifact image from the needleless image according to the plurality of multi-scale features; and the processor removing the artifact image from the needleless image to generate an artifactless image;

wherein the needle body positioning information includes a reference position, a length, and/or a width corresponding to the needle body of at least one predetermined insertion angle.

8. The method of claim 7,
wherein the first convolutional neural network and the second convolutional neural network are homogeneous neural networks or heterogeneous neural networks.

9. The method of claim 7, further comprising:
the processor acquiring a plurality of multi-scale features from the trained first convolutional neural network, and
the processor enhancing the target image according to the plurality of multi-scale features and the needle body positioning information of the target image to generate an enhanced target image.

10. The method of claim 7, further comprising:
the processor acquiring a plurality of multi-scale features from the trained second convolutional neural network; and
the processor enhancing the needle tip in the target image according to the plurality of multi-scale features and the needle tip positioning information of the target image to generate an enhanced needle tip image.

11. The method of claim 10, further comprising:
the processor computing a linear combination of the plurality of multi-scale features to optimize the enhanced needle tip image.

* * * * *